United States Patent [19]

Ferguson et al.

[11] Patent Number: 5,430,168

[45] Date of Patent: Jul. 4, 1995

[54] ALUMIMUM TRICHLORIDE CATALYZED HYDROGENATION OF HIGH-BOILING RESIDUE FROM DIRECT PROCESS

[75] Inventors: Stephen P. Ferguson, Louisville; Robert F. Jarvis, Jr., Union, both of Ky.; Brian M. Naasz, De Witt, Mich.; Kimberly K. Oltmanns, LaGrange; Gordon L. Warrick, Carrollton; Darrel L. Whiteley, LaGrange, all of Ky.

[73] Assignee: Dow Corning Corporation, Midland, Mich.

[21] Appl. No.: 329,758

[22] Filed: Oct. 27, 1994

[51] Int. Cl.$^6$ ............................................. C07F 7/08
[52] U.S. Cl. ................................. 556/467; 556/468
[58] Field of Search ............................. 556/467, 468

[56] References Cited

U.S. PATENT DOCUMENTS

| | | | |
|---|---|---|---|
| 2,380,995 | 8/1945 | Rochow | 260/607 |
| 2,488,487 | 11/1949 | Barry et al. | 260/448.2 |
| 2,598,435 | 5/1952 | Mohler et al. | 260/448.2 |
| 2,606,811 | 8/1952 | Wagner | 12/14 |
| 2,681,355 | 6/1954 | Barry et al. | 260/448.2 |
| 3,639,105 | 2/1972 | Atwell et al. | 23/366 |
| 4,070,071 | 3/1978 | Neale | 260/448.2 E |
| 4,393,229 | 7/1983 | Ritzer et al. | 556/430 |
| 5,175,329 | 12/1992 | Bokerman et al. | 556/467 |
| 5,288,892 | 2/1994 | Pachaly et al. | 556/468 X |
| 5,292,909 | 3/1994 | Chadwick et al. | 556/468 |
| 5,292,912 | 3/1994 | Chadwick et al. | 556/468 |
| 5,321,147 | 6/1994 | Chadwick et al. | 556/468 X |
| 5,326,896 | 7/1994 | Chadwick et al. | 556/468 X |

*Primary Examiner*—Paul F. Shaver
*Attorney, Agent, or Firm*—William F. Boley

[57] ABSTRACT

A process for the production of monosilanes from the high-boiling residue resulting from the reaction of organohalides with silicon metalloid in a process typically referred to as the "direct process." The present process comprises forming a mixture comprising an organotrihalosilane and the high-boiling residue in the presence of hydrogen gas and a catalytic amount of aluminum trichloride. The present process results in consumption of the organotrihalosilane rather than a net increase which typically occurs in processes for hydrogenation of the high-boiling residue. At least a portion of the catalytic amount of aluminum trichloride may be formed in situ during conduct of the direct process and isolation of the high-boiling residue.

17 Claims, No Drawings

ALUMIMUM TRICHLORIDE CATALYZED HYDROGENATION OF HIGH-BOILING RESIDUE FROM DIRECT PROCESS

BACKGROUND OF INVENTION

The present invention is a process for the production of monosilanes from the high-boiling residue resulting from the reaction of organohalides with silicon metalloid in a process typically referred to as the "direct process." The present process comprises forming a mixture comprising an organotrihalosilane and the high-boiling residue in the presence of hydrogen gas and a catalytic amount of aluminum trichloride. The present process results in consumption of the organotrihalosilane rather than a net increase which typically occurs in processes for hydrogenation of the high-boiling residue. At least a portion of the catalytic amount of aluminum trichloride may be formed in situ during conduct of the direct process and isolation of the high-boiling residue.

In the preparation of organohalosilanes by the direct process a complex mixture is formed which is typically distilled to separate monosilanes from other components present in the mixture. For example, in the "direct process," in addition to the monosilanes which in the case of the chloromonosilanes include dimethyldichlorosilane, methyltrichlorosilane, and trimethylchlorosilane there is obtained a residue which boils above the organohalosilanes, that is above about 70° C. This residue is hereinafter referred to as "high-boiling residue."

The "direct process" is well described in the patent literature, for example, in Rochow, U.S. Pat. No. 2,380,995, issued Aug. 7, 1945, and Barry et al., U.S. Pat. No. 2,488,487, issued Nov. 15, 1949. The residue remaining after distillation overhead of the monosilanes is a complex mixture comprising higher boiling silicon containing compounds which have, for example, SiSi, SiOSi, and SiCSi linkages in the molecules. The residue may also contain silicon particulates and metals or compounds thereof. Typical high-boiling residues obtained from distillation of product from the direct process are described, for example, in Mohler et al., U.S. Pat. No. 2,598,435, issued May 27, 1952, and Barry et al., U.S. Pat. No. 2,681,355, issued Jun. 15, 1954.

In current commercial operations for performing the direct process, the high-boiling residue can constitute as much as five weight percent of the resultant product. Therefore, it is desirable to convert the high-boiling residue into commercially desirable products to both reduce waste disposal and to improve raw material utilization.

Wagner, U.S. Pat. No. 2,606,811, issued Aug. 12, 1952, teaches a hydrogenation process where a compound containing a halogen and the Si—Si bond is heated to a temperature of at least 300° C. in the presence of hydrogen. The resultant products are monosilanes.

Atwell et al., U.S. Pat. No. 3,639,105, issued Feb. 1, 1972, describe a process where hydrosilanes are produced by contacting a disilane with hydrogen gas under pressure and heating the mixture in the presence of a transition metal catalyst such as palladium on charcoal. Atwell et al. state that the disilane may be part of a mixture from the direct process. Atwell et al. further report that when the disilane was a methylchlorosilane, the resulting product contained about four to 28 weight percent of methyltrichlorosilane. Generally, organotrihalosilanes such as methyltrichlorosilane have limited commercial usefulness and for this reason limit the usefulness of the process described by Atwell et al.

Neale, U.S. Pat. No. 4,079,071, issued Mar. 14, 1978, describes a process for preparing high yields of hydrosilanes by reacting methylchloropolysilanes with hydrogen gas under pressure at a temperature of from 25° C. to about 350° C. in the presence of a copper catalyst. Neale states that the methylchloropolysilanes can be those typically created as by-products of the direct process. Useful copper catalysts described by Neale include copper metal, copper salts, and complexes of copper salts with organic ligands. In some cases, Neale reports that up to 29 weight percent of methyltrichlorosilane was formed.

Ritzer et al., U.S. Pat. No. 4,393,229, issued Jul. 12, 1983, describe a process for converting alkyl-rich disilanes in a residue obtained from the manufacture of alkylhalosilanes to halogen-rich polysilanes. The process comprises treating an alkyl-rich disilane-containing residue with an alkyltrihalosilane or silicon tetrahalide in the presence of a catalyst and a catalytic amount of a hydrosilane reaction promoter at an elevated temperature. Ritzer et al. teach aluminum trichloride as a useful catalyst in their process when used with a hydrosilane promoter. Ritzer et al. further teach that the resulting halogen-rich polysilanes can, in a separate step, be cleaved to form monosilanes.

Bokerman et al., U.S. Pat. No. 5,175,329, describe a process for the production of organosilanes from the high-boiling residue resulting from the direct process that results in a net consumption of organotrichlorosilane. In the described process the high-boiling residue is contacted with an organotrichlorosilane and hydrogen gas in the presence of both a hydrogenation catalyst and a redistribution catalyst.

An object of the present invention is to provide a simple process where the high-boiling residue from a direct process for producing organohalosilanes can be converted into commercially useful monosilanes while resulting in a net consumption of organotrihalosilane. The present inventors have discovered that this objective can be met by contacting the high-boiling residue with an organotrihalosilane, hydrogen gas, and a catalytic amount of aluminum trichloride at a temperature within a range of about 150° C. to 500° C. Furthermore, at least a portion of the catalytic amount of aluminum trichloride can be formed in situ during conduct of the direct process and isolation of the resulting monosilanes.

SUMMARY OF INVENTION

The present invention is a process for the production of monosilanes from the high-boiling residue resulting from the reaction of organohalides with silicon metalloid in a process typically referred to as the "direct process." The present process comprises forming a mixture comprising an organotrihalosilane and the high-boiling residue in the presence of hydrogen gas and a catalytic amount of aluminum trichloride. The present process results in consumption of the organotrihalosilane rather than a net increase which typically occurs in processes for hydrogenation of the high-boiling residue. At least a portion of the catalytic amount of aluminum trichloride may be formed in situ during conduct of the direct process and isolation of the high-boiling residue.

DESCRIPTION OF INVENTION

The present invention is a process for converting a high-boiling residue resulting from the reaction of an organohalide with silicon metalloid to monosilanes. The process comprises:

(A) forming a mixture comprising a high-boiling residue resulting from the reaction of an organohalide with silicon metalloid and an organotrihalosilane described by formula $$RSiX_3, \tag{1}$$

where R is selected from a group consisting of alkyls comprising one to six carbon atoms, aryls, alkoxys comprising one to six carbon atoms, trimethylsilyl, and trifluoropropyl and X is halogen; and (B) contacting the mixture with hydrogen gas at a pressure of about 50 psig to 10,000 psig in the presence of a catalytic amount of aluminum trichloride at a temperature within a range of about 150° C. to 500° C.

The present process can further comprise:

(C) recovering organosilanes of formula $$R_yH_zSiX_{4-y-z}, \tag{2}$$

where R and X are as described above, y=0 to 3, z=0 to 3 and y+z=0 to 3.

The present process may be run in any standard pressurizable reactor suitable for contact with halosilanes. The process may be run as a batch process or as a continuous process. The process may be run, for example, in a stirred-bed reactor, continuous stirred-tank reactor, a bubble-column reactor, a trickle-bed reactor, or a plug-flow reactor.

The present process is useful for converting a high-boiling residue resulting from the reaction of an organohalide with silicon metalloid to useful monosilanes. In a typical process for reacting an organohalide with silicon metalloid, the process is conducted at a temperature of about 300° C. to 350° C. in the presence of suitable catalysts and gaseous product and feed along with fine particulates are continuously removed from the process. The removed materials are subsequently distilled to recover organohalosilanes, leaving a "high-boiling residue."

A preferred high-boiling residue for use in the present process is one with a boiling point above about 70° C. resulting from the distillation of organohalosilanes from the reaction product of methyl chloride with silicon metalloid. A typical composition for such a high-boiling residue comprises: 50–60 wt % of disilanes of formula $Si_2Q_6$, where each Q is independently selected from a group consisting of methyl and chlorine and the disilane contains two to four methyl substituents per molecule; 15 to 25 weight percent silmethylenes described by formula $Q_3SiCH_2SiQ_3$, where Q is as previously described and the silmethylene contains two to four methyl substituents per molecule; silalkylenes described by formula $Q_3Si(SiQ_2)_a(CH_2)_b(SiQ_2)_cSiQ_3$, where Q is as previously described, the silalkylene contains two to four methyl substituents per molecule, a=0 to 4, b=1 to 3, c=0 to 4, and a+c≧1; 5 to 15 weight percent other high-boiling silicon-containing compounds; catalysts carry over from the direct process such as copper and compounds of copper; particulates containing silicon; and low levels of metals such as aluminum, calcium, and iron and compounds thereof.

As previously discussed, it is known that the high-boiling residue can be treated with a hydrogenation catalyst and hydrogen gas to produce monosilanes. However, a consequence of this hydrogenation process is the production of organotrihalosilanes which have limited commercial utility and therefore are an undesirable product. Bokerman et al., supra, describe a hydrogenation process for converting disilanes into monosilanes that resulted in a net consumption of organotrihalosilane, but required both a hydrogenation catalyst and a redistribution catalyst. Unexpectly, the present inventors have discovered a process for converting a high-boiling residue to monosilanes that results in the consumption of organotrihalosilane and appears to require only aluminum trichloride as catalyst. However, the present inventors do not intend to preclude the possible presence of other materials in the high-boiling residue which also may also be active as catalyst, co-catalyst, promotor, or the like in the present claimed process.

In the present process a mixture of the high-boiling residue as described above is formed with an organotrihalosilane as described by formula (1). The mixture can be formed external to the reactor and added to the reactor or may be formed by adding the individual components to the reactor. The organotrihalosilane contains one substituent R, where R is selected from a group consisting of alkyls comprising one to six carbon atoms, aryls, alkoxys comprising one to six carbon atoms, trimethylsilyl, and trifluoropropyl. Substituent R can be, for example, methyl, ethyl, propyl, isopropyl, tert-butyl, methoxy, ethoxy, phenyl, tolyl, naphthyl, trimethylsilyl, and trifluoropropyl. Preferred is when R is methyl.

The organotrihalosilane contains three halogen substituents, X, where X can be any halogen. Preferred is when X is chlorine. The organotrihalosilane can be, for example, methyltrichlorosilane, ethyltrichlorosilane, benzyltrichlorosilane, methyltribromosilane, methyltriiodosilane, and methyltrifluorosilane. Preferred is when the organotrihalosilane is methyltrichlorosilane.

The weight percent of organotrihalosilane in the mixture with the high-boiling residue is not critical to the present process. Generally, a mixture where the organotrihalosilane is about 0.1 to 95 weight percent of the mixture is considered useful. Preferred is where the organotrihalosilane is about 30 to 50 weight percent of the mixture.

The mixture is contacted with hydrogen gas at a pressure of about 50 psig to 10,000 psig. Preferred is a hydrogen gas pressure of about 300 psig to 1500 psig. More preferred is a hydrogen gas pressure of about 600 psig to 1100 psig.

The mixture, in the presence of hydrogen gas, is contacted with a catalytic amount of aluminum trichloride. By "catalytic amount" it is meant an amount of aluminum trichloride sufficient to facilitate the conversion of silicon containing compounds in the high-boiling residue to monosilanes. A preferred catalytic amount of aluminum trichloride is that sufficient to facilitate the conversion of polysilanes, for example methylchlorodisilanes, silmethylenes, and silalkylenes in the high-boiling residue to monosilanes. Generally, about 0.01 to 10 weight percent of aluminum trichloride, based on the combined weight of the aluminum trichloride and the high-boiling residue is considered useful in the present process. Preferred is when about 0.1 to 2.0 weight percent of aluminum trichloride, on the same basis, is present in the process.

The aluminum trichloride may be added to the process as the compound or may be formed in situ by the addition of materials that form aluminum trichloride. All or a portion of the catalytic amount of aluminum trichloride may be formed in situ during conduct of the direct process and isolation of the monosilane fraction to form the high-boiling fraction. The source of the aluminum and chlorine necessary to form the aluminum trichloride can be the raw materials used in the direct process, particularly the silicon metalloid and organohalide feed. The catalytic amount of aluminum trichloride can be a combination of added aluminum trichloride and that in situ formed aluminum trichloride remaining in the high-boiling residue as isolated from the direct process.

The present process can be conducted at a temperature within a range of about 150° C. to 500° C. Preferred is a temperature within a range of about 275° C. to 425° C. Most preferred is a temperature within a range of about 300° C. to 350° C.

Monosilanes as described by formula (2) are recovered from the present process. The monosilanes can be separated by standard methods for separating liquid mixtures, for example, distillation. The monosilanes can contain zero to three substituents R, where R is as previously described. The monosilane can contain zero to three hydrogens substituted on each silicon atom. The monosilanes can contain one to four halogens substituted on each silicon atom. A preferred monosilane is selected from a group consisting of dimethyldichlorosilane and methyldichlorosilane.

The following examples are provided to illustrate the present invention. These examples are not intended to limit the claims herein.

Example 1

The ability of aluminum trichloride to catalyze the hydrogenation of a high-boiling residue (HBR) was evaluated in a stirred-batch reactor. The reactor was a 450 ml, pneumatically stirred, Parr Bomb reactor. About 0.15 mole (Mol) of a high boiling residue from a direct process for the preparation of methylchlorosilanes by the reaction of methyl chloride with silicon metalloid was added to the reactor. The high-boiling residue was the fraction remaining in the bottom of a still after distilling off the monosilane fraction at about 70° C. The high-boiling residue was filtered to reduce particulates and adsorbed twice with about equal volumes of activated carbon. Elemental metals analysis of the adsorbed high-boiling residue showed the presence of 0.0082 weight percent aluminum. A typical composition along with a range for major silicon containing compounds found in the filtered high-boiling residue is provided in Table 1.

TABLE 1

| Composition of High-Boiling Residue | | |
|---|---|---|
| Component | Weight % | Range (Wt %) |
| $MeCl_2SiOSiCl_2Me$ | 2 | 0–5 |
| $Me_2ClSiSiClMe_2$ | 3 | 0–9 |
| $Me_2ClSiSiMeCl_2$ | 22 | 10–40 |
| $MeCl_2SiSiMeCl_2$ | 32 | 20–50 |
| $Me_2ClSiCH_2SiClMe_2$ | 2 | 0–9 |
| $Me_2ClSiCH_2SiCl_2Me$ | 5 | 0–15 |
| $MeCl_2SiCH_2SiCl_2Me$ | 10 | 5–20 |
| $Me_3SiCl$ | 0 | 0–4 |

TABLE 1-continued

| Composition of High-Boiling Residue | | |
|---|---|---|
| Component | Weight % | Range (Wt %) |
| $MeHSiCl_2$ | 0 | 0–2 |
| $EtMeSiCl_2$ | 2 | 0–5 |
| $iPrMeSiCl_2$ | 1 | 0–5 |
| Non-elutables | 21 | 10–40 |

In Table 1, Me is methyl, Et is ethyl, iPr is isopropyl, and non-elutables are those materials which do not elute from the GC column.

Two runs were made, the first run was a base run without the addition of aluminum trichloride and in the second run 0.55 weight percent of aluminum chloride, based on high boiling residue weight, was added to the reactor. The amount of hydrogen gas and methyltrichlorosilane (Mono) added to the reactor for each run is provided in Table 2. For each run, the reactor was heated to about 325° C. and stirred for about 2.8 hours. At the end of each run a sample from the reactor was analyzed by gas chromatography (GC) using a thermal conductivity detector (TCD). The results of this analysis are reported in Table 2. In Table 2, the "Total silane Yield" is calculated as the weight silane in the product minus the weight of methyltrichlorosilane added to the process, the difference divided by the weight of HBR added to the process, the dividend multiplied by 100. "HBR Conversion" is reported as weight percent of HBR converted to product. Also, reported in Table 2 is the weight percent of silmethylene conversion, disilane conversion, and high-boiling species conversion to other products. The weight percent conversion of methyltrichlorosilane to other products is reported in Table 2 in the row labelled "Mono. Conv." A positive number for methyltrichlorosilane conversion indicates a consumption of methyltrichlorosilane in the process.

The product distribution for each run is present in Table 2 in the columns labelled "Net Monosilane Product Distribution." The net monosilane product distribution is calculated as the weight percent each species of monosilane represents of the total monosilanes present in the product after subtracting out the amount of methyltrichlorosilane present in the product.

TABLE 2

| Aluminum Trichloride Catalyzed Hydrogenation of HBR | | |
|---|---|---|
| | Run 1 | Run 2 |
| Temp. (°C.) | 325 | 325 |
| Pressure (psig) | 1333 | 1252 |
| Time (h) | 2.8 | 2.8 |
| Catalyst (wt. %) | — | 0.55 |
| Mono (mole) | 0.15 | 0.15 |
| HBR (mole) | 0.15 | 0.18 |
| Hydrogen (mole) | 0.95 | 0.92 |
| Total Silane Yield | 17.3 | 83.2 |
| HBR Conv. | 36.7 | 91.0 |
| Disilane Conv. | 37.0 | 98.9 |
| Silmethylene Conv. | 14.1 | 54.9 |
| Non-elutables Conv. | 32.3 | 70.9 |
| Mono Conv. | 0.0 | 18.6 |
| Net Monosilane Product Distribution (Wt %) | | |
| $MeH_2SiCl$ | 7.0 | 8.9 |
| $Me_4Si$ | 0.0 | 0.0 |
| $HSiCl_3$ | 1.4 | 4.0 |
| $Me_2HSiCl$ | 9.5 | 3.1 |
| $MeHSiCl_2$ | 48.8 | 57.1 |
| $SiCl_4$ | 0.5 | 0.1 |
| $Me_3SiCl$ | 2.2 | 0.9 |
| $Me_2SiCl_2$ | 30.2 | 25.9 |

Example 2

The effect of in situ formed aluminum trichloride on the hydrogenation of a high-boiling residue in a stirred-batch reactor was evaluated. The reactor was the same as described in Example 1. About 0.13 mole of a high-boiling residue resulting from the reaction of methyl chloride with silicon metalloid and boiling above about 70° C. was added to the reactor. The high-boiling residue was filtered to reduce particulates and had a composition similar to that described in Table 1. For comparison purposes, a sample of the high-boiling residue was adsorbed twice with about an equal volume of activated charcoal and the testing of this material is reported in Table 3 as Run 3. After adsorption, the elemental analysis of the high-boiling residue showed the presence of 0.0003 weight percent aluminum. Elemental analysis of the test sample (Run 4) showed the presence of about 0.76 weight percent aluminum. The conditions under which the test and comparison runs were made are described in Table 3. The product from the two runs was analyzed by GC-TCD. The results are reported in Table 3. The headings for Table 3 are as described for Table 2.

TABLE 3

In Situ Formed Aluminum Trichloride Catalyzed Hydrogenation of HBR

|  | Run 3 | Run 4 |
|---|---|---|
| Temp. (°C.) | 325 | 325 |
| Pressure (psig) | 1046 | 1056 |
| Time (h) | 1.0 | 1.0 |
| Mono (mole) | 0.13 | 0.13 |
| HBR (mole) | 0.13 | 0.13 |
| Hydrogen (mole) | 0.60 | 0.60 |
| Total Silane Yield | 0.0 | 100.0 |
| HBR Conv. | 39.0 | 89.6 |
| Disilane Conv. | 25.9 | 93.1 |
| Silmethylene Conv. | 9.6 | 30.1 |
| Mono Conv. | 5.2 | 28.8 |
| Net Monosilane Product Distribution (Wt %) |  |  |
| $MeH_2SiCl$ | 0.0 | 5.6 |
| $Me_4Si$ | 0.0 | 0.0 |
| $HSiCl_3$ | 0.0 | 3.2 |
| $Me_2HSiCl$ | 0.0 | 3.1 |
| $MeHSiCl_2$ | 5.5 | 48.6 |
| $SiCl_4$ | 3.4 | 0.3 |
| $Me_3SiCl$ | 8.8 | 0.7 |
| $Me_2SiCl_2$ | 82.3 | 38.3 |

We claim:

1. A process for converting a high-boiling residue resulting from the reaction of an organohalide with silicon metalloid to monosilanes, the process comprising:
   (A) forming a mixture comprising a high-boiling residue resulting from the reaction of an organohalide with silicon metalloid and an organotrihalosilane described by formula $RSiX_3$, where R is selected from a group consisting of alkyls comprising one to six carbon atoms, aryls, alkoxys comprising one to six carbon atoms, trimethylsilyl, and trifluoropropyl and X is halogen; and
   (B) contacting the mixture with hydrogen gas at a pressure of about 50 psig to 10,000 psig in the presence of a catalyst consisting essentially of aluminum trichloride at a temperature within a range of about 150° C. to 500° C.

2. A process according to claim 1 further comprising (C) recovering monosilanes of formula $R_yH_zSiX_{4-y-z}$ where R and X are as previously described, y=0 to 3, z=0 to 3, and y+z=0 to 3.

3. A process according to claim 2, where the monosilane is selected from a group consisting of dimethyldichlorosilane and methyldichlorosilane.

4. A process according to claim 1, where the high-boiling residue has a boiling point above about 70° C. and is a distillation fraction resulting from the distillation of the reaction product of methyl chloride with silicon metalloid.

5. A process according to claim 4, where the organotrihalosilane is methyltrichlorosilane.

6. A process according to claim 1, where the organotrihalosilane is about 0.1 to 95 weight percent of the mixture comprising the high-boiling residue and the organotrihalosilane.

7. A process according to claim 1, where the organotrihalosilane is about 30 to 50 weight percent of the mixture comprising the high-boiling residue and the organotrihalosilane.

8. A process according to claim 1, where the hydrogen gas pressure is in a range of about 300 psig to 1500 psig.

9. A process according to claim 1, where the hydrogen gas pressure is in a range of about 600 psig to 1100 psig.

10. A process according to claim 1, where about 0.01 to 10 weight percent of aluminum trichloride, based on the combined weight of the aluminum trichloride and the high-boiling residue, is present in the process.

11. A process according to claim 1, where about 0.1 to 2.0 weight percent of aluminum trichloride, based on the combined weight of the aluminum trichloride and the high-boiling residue, is present in the process.

12. A process according to claim 1, where a portion of the catalytic amount of aluminum trichloride is formed in situ during formation of the high-boiling residue.

13. A process according to claim 1, where the temperature is within a range of about 275° C. to 425° C.

14. A process according to claim 1, where the temperature is within a range of about 300° C. to 350° C.

15. A process for converting a high-boiling residue resulting from the reaction of methyl chloride with silicon metalloid to monosilanes, the process comprising:
   (A) forming a mixture comprising a high-boiling residue resulting from the reaction of methyl chloride with silicon metalloid, where the high-boiling residue is a distillation fraction having a boiling point above about 70° C., with methyltrichlorosilane where methyltrichlorosilane is 30 to 50 weight percent of the mixture; and
   (B) contacting the mixture with hydrogen gas at a pressure of about 600 psig to 1100 psig in the presence of a catalyst consisting essentially of 0.1 to 2.0 weight percent aluminum trichloride, based upon the combined weight of the aluminum trichloride and the high-boiling residue, at a temperature within a range of about 300° C. to 350° C.

16. A process according to claim 15 further comprising recovering monosilanes selected from a group consisting of dimethyldichlorosilane and methyldichlorosilane.

17. A process according to claim 1, where the catalyst consists of aluminum trichloride.

* * * * *